United States Patent
Lang

(10) Patent No.: US 9,922,542 B2
(45) Date of Patent: Mar. 20, 2018

(54) FIRE DETECTOR TEST DEVICE AND METHODS THEREFOR

(71) Applicant: Honeywell International Inc., Morristown, NJ (US)

(72) Inventor: Scott Robert Lang, Geneva, IL (US)

(73) Assignee: HONEYWELL INTERNATIONAL INC., Morristown, NJ (US)

( * ) Notice: Subject to any disclaimer, the term of this patent is extended or adjusted under 35 U.S.C. 154(b) by 0 days.

(21) Appl. No.: 15/099,741

(22) Filed: Apr. 15, 2016

(65) Prior Publication Data

US 2017/0301226 A1     Oct. 19, 2017

(51) Int. Cl.
G08B 29/14     (2006.01)
A61M 21/00     (2006.01)

(52) U.S. Cl.
CPC .......... G08B 29/145 (2013.01); G08B 29/14 (2013.01); *A61M 21/00* (2013.01); *G01N 2291/0217* (2013.01)

(58) Field of Classification Search
CPC .............. G08B 29/145; G08B 29/14; G01N 2291/0217; A61M 21/00
See application file for complete search history.

(56) References Cited

U.S. PATENT DOCUMENTS

| | | | |
|---|---|---|---|
| 5,670,946 A * | 9/1997 | Ellwood | G08B 29/145 222/402.13 |
| 6,015,230 A | 1/2000 | Wantz et al. | |
| 2004/0194083 A1 * | 9/2004 | Hindle | G06F 8/61 717/174 |
| 2009/0308134 A1 * | 12/2009 | Pepper | G08B 29/12 73/1.06 |

(Continued)

FOREIGN PATENT DOCUMENTS

| | | |
|---|---|---|
| EP | 1 286 320 A2 | 2/2003 |
| EP | 2 711 907 A1 | 3/2014 |

(Continued)

OTHER PUBLICATIONS

Extended European search report from corresponding EP patent application 17162977.7, dated Oct. 2, 2017.

(Continued)

*Primary Examiner* — Mohamed Barakat
(74) *Attorney, Agent, or Firm* — Husch Blackwell LLP

(57) ABSTRACT

An improved fire detector test device and methods for conducting field sensitivity and functionality testing of a fire detector in-situ are provided. The test device can include ambient condition or stimulus generating devices and a programmable processor, wherein the programmable processor can identify information about a detector under test, wherein the programmable processor can obtain a configuration file based on the identified information about the detector under test, wherein the configuration file can identify a combination, level, or rate of a plurality of stimuli that cause an alarm in the detector under test, and wherein the programmable processor can execute the configuration file to cause the ambient condition or stimulus generating devices to generate and emit the plurality of stimuli in the combination and at the level and the rate identified in the configuration file.

12 Claims, 2 Drawing Sheets

(56) References Cited

U.S. PATENT DOCUMENTS

2014/0269386 A1* 9/2014 Chu ................. H04L 41/145
                                                370/252
2015/0077242 A1* 3/2015 Simoncic ............ G08B 29/12
                                                340/514
2016/0203704 A1* 7/2016 Williams ........... G08B 29/145
                                                340/515

FOREIGN PATENT DOCUMENTS

GB   2 432 703 A    5/2007
WO   94/18653 A1    8/1994

OTHER PUBLICATIONS

English-language translation of Abstract for EP patent application publication 1 286 320 A2, dated Feb. 26, 2003.
English-language translation of Abstract for EP patent application publication 2 711 907 A1, dated Mar. 26, 2014.

* cited by examiner

FIRE DETECTOR TEST DEVICE AND METHODS THEREFOR

FIELD

The present invention relates generally to a fire detector test device. More particularly, the present invention relates to an improved fire detector test device and methods therefor.

BACKGROUND

The National Fire Protection Agency (NFPA) creates and maintains standards, for example, NFPA 72, which is the National Fire Alarm and Signaling Code and requires field sensitivity and functionality testing of fire detectors on a regular basis. Such testing ensures that contaminants have not built up in a detector or that a detector has not been exposed to contaminants that may affect the detector properly detecting fire.

Field sensitivity and functionality testing is different than functional or go/no-go testing, which can be performed via a test switch on a detector or via an unmeasured concentration of an ambient condition that can be sprayed into a detector. For example, functional or go/no-go testing only verifies that a detector is capable of generating an alarm, that an ambient condition can enter a sensing chamber, and that a detector can notify a fire alarm control panel about an alarm. However, functional or go/no-go testing does not verify the sensitivity or proper alarm level of a detector.

Test devices for conducting field sensitivity and functional testing on fire detectors are known in the art. A single criteria fire detector can be responsive to a signal from a single type of sensor such as, for example, a smoke sensor, a heat sensor, or a gas sensor, such as a carbon monoxide sensor. Accordingly, a test device for a single criteria fire detector can expose the detector to a known concentration of a single ambient condition to initiate an alarm in the detector.

For example, some known testing devices include an aerosol generating device and a cup that can be placed over a detector. The generating device can generate a known concentration of an ambient condition, such as smoke, heat, or gas, which can be directed to the detector via the cup. Upon detecting an amount or concentration of the ambient condition above a predetermined threshold, the detector can initiate an alarm.

Unlike with single criteria fire detectors, it is difficult to test the field sensitivity and functionality of multi-criteria fire detectors because such detectors use complex algorithms to combine signals from multiple sensors, such as, for example, a smoke sensor, a heat sensor, and a gas sensor, such as a carbon monoxide sensor, to determine when to initiate an alarm. Accordingly, exposing a multi-criteria fire detector to only a single ambient condition, as when testing a single criteria fire detector, may not initiate an alarm in the multi-criteria fire detector.

Test devices for multi-criteria fire detectors are known and can generate a plurality of different ambient conditions, such as, smoke, heat, and gas, but such devices may not generate the ambient conditions in a combination and at such as rate so as to initiate an alarm in a fire detector. Indeed, known test devices may not know the combination and rate of ambient conditions required by an algorithm used by the detector to initiate the alarm. Furthermore, different manufacturers of fire detectors may use different algorithms to combine signals from multiple sensors. Accordingly, a test device that works for one fire detector may not work for another fire detector.

In view of the above, there is a continuing, ongoing need for improved test devices.

DETAILED DESCRIPTION

Figure 1:
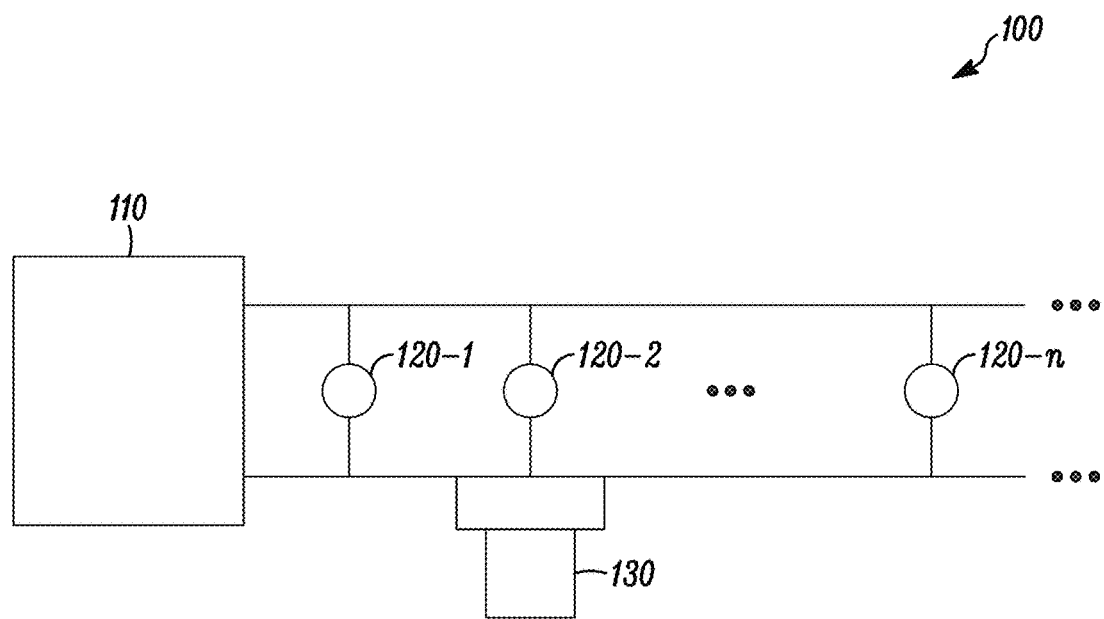
FIG. 1 is a block diagram of a system in accordance with disclosed embodiments.

While this invention is susceptible of an embodiment in many different forms, there are shown in the drawings and will be described herein in detail specific embodiments thereof with the understanding that the present disclosure is to be considered as an exemplification of the principles of the invention. It is not intended to limit the invention to the specific illustrated embodiments.

Embodiments disclosed herein can include an improved fire detector test device and methods for conducting field sensitivity and functionality testing of a fire detector in-situ. For example, a fire detector test device as disclosed herein can execute a configuration file that instructs the test device how to generate ambient conditions and stimuli, such as, for example, smoke, heat, and gas, including in what combination and at what level and build-up rate, so as to initiate or cause an alarm in a fire detector under test.

It is known that a fire detector, such as a multi-criteria fire detector, may have a plurality of different paths to generating an alarm such that the detector may generate an alarm responsive to a plurality of ambient conditions or stimuli in a plurality of different combinations. For example, a fire detector may initiate or cause an alarm responsive to detecting a first amount of smoke, no heat, and an amount of gas rising at a first rate or responsive to detecting a second amount of smoke, an amount of heat rising at a second rate, and no gas. The configuration file as disclosed herein can identify the ambient conditions and the combinations thereof that cause a detector to initiate an alarm, and the test device can execute the configuration file to test the functionality and sensitivity of the detector accordingly, for example, by generating each of the identified ambient conditions or stimuli, for example, smoke, heat, and gas, in the identified combinations thereof. In some embodiments, the test device as disclosed herein can include a cup or other device for enclosing a space around a fire detector, and the test device can generate each of the identified ambient conditions or stimuli in the identified combinations into the enclosed space for detection by the fire detector.

In some embodiments, the test device as disclosed herein can include a wired or wireless transceiver for receiving a downloaded configuration file and a memory device for storing the downloaded configuration file therein. In some embodiments, the configuration file can be downloaded to the test device based on the type and manufacturer of a fire detector under test so that the test device can execute a configuration file specific to the fire detector under test. For example, the test device can identify the type and manufacturer of a fire detector under test and can download an appropriate configuration file based on the identified type and manufacturer of the fire detector under test. In some embodiments, the configuration file can be downloaded to the test device from a fire detector under test, from a control panel in communication with a fire detector under test, or from a manufacturer of a fire detector under test, for example, a cloud server operated by the manufacturer.

In some embodiments, the configuration file can identify the type and manufacturer of a fire detector under test, and the test device can identify or obtain the configuration file or a combination, level, and rate of ambient conditions or stimuli to generate based on the identified type and manufacturer. In some embodiments, the test device can identify the type and manufacturer of a fire detector under test based on a signal received from the fire detector under test or a control panel in communication with a fire detector under test, where such a signal is different from a signal that transmits the configuration file. In some embodiments, the test device can identify the type and manufacturer of a fire detector under test based on an image or scan of all or a portion of the fire detector under test. In some embodiments, the test device can receive user input identifying the type and manufacturer of a fire detector under test.

In some embodiments, the test device disclosed herein can download an updated version of the configuration file, when available, prior to execution thereof. For example, the test device can connect to the internet via its wireless transceiver to identify when an update to the configuration filed stored in a local memory device is available and download such update when appropriate.

In some embodiments, the configuration file downloaded to the test device as disclosed herein can include proprietary information of the manufacturer of a fire detector. Because the test device as disclosed herein can test fire detectors from a plurality of different manufacturers, any proprietary information in the configuration file can remain protected, even when the configuration file is downloaded to the test device, for example, by encrypting the configuration file.

Systems and methods disclosed herein are described in connection with a fire detector. However, it is to be understood that systems and methods are not so limited and can be used in connection with any detector as would be understood by one of ordinary skill in the art, including, but not limited to a fire detector, a heat detector, a smoke detector, a gas detector, and a single criteria or multi-criteria detector of any such type of detector.

FIG. 1 is a block diagram of a system 100 in accordance with disclosed embodiments. As seen in FIG. 1, the system 100 can include a plurality of detectors 120 in communication with a control panel 110. Prior to conducting a field sensitivity and functionality test of a detector 120, a test device 130 can identify information about the detector 120, for example, the type, manufacturer, or address of the detector 120 and download a configuration file based on the identified type, manufacturer, or address of the detector 120. The downloaded configuration file can instruct the test device 130 how to generate ambient conditions and stimuli, including in what combination and at what level and build-up rate, so as to initiate or cause an alarm in the detector 120.

To conduct the test of the detector 120, the test device 130 can be placed within a predetermined proximity of the detector 120 and execute the downloaded configuration file, thereby causing the test device 130 to generate and emit the ambient conditions and stimuli identified by the configuration file in the combination and at the level and build-up rate identified by the configuration file.

Figure 2:
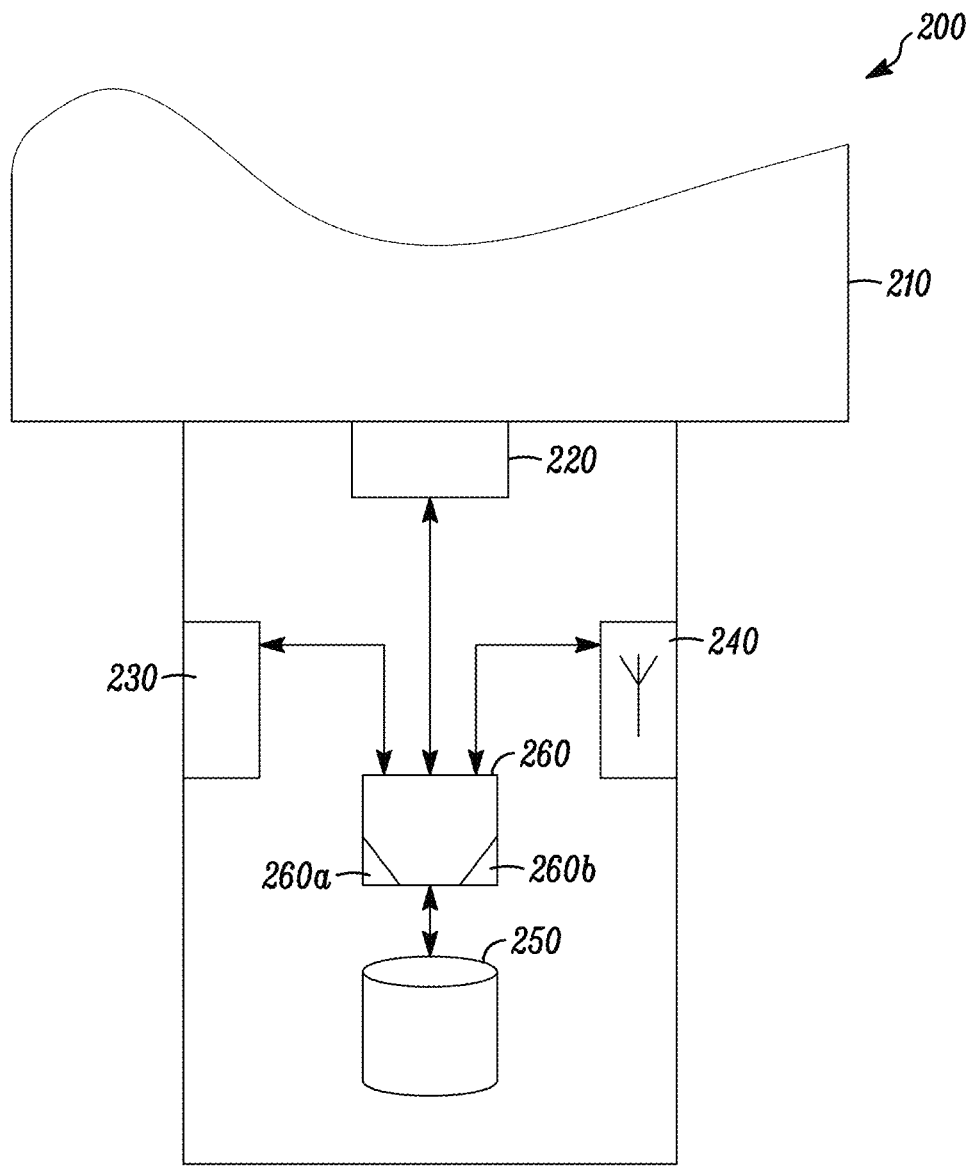
FIG. 2 is a block diagram of a test device in accordance with disclosed embodiments.

FIG. 2 is a block diagram of a test device 200 in accordance with disclosed embodiments. As seen in FIG. 2, the test device 200 can include a cup 210, one or more ambient condition or stimulus generating devices 220, a user interface device 230, a wired or wireless transceiver 240, and a memory device 250, each of which can be in communication with control circuitry 260, one or more programmable processors 260a, and executable control software 260b as would be understood by one or ordinary skill in the art. The executable control software 260b can be stored on a transitory or non-transitory computer readable medium, including, but not limited to local computer memory, RAM, optical storage media, magnetic storage media, flash memory, and the like. In some embodiments, some or all of the control circuitry 260, programmable processor 260a, and control software 260b can execute and control the methods described above and herein.

For example, in some embodiments, the user interface device 230, the transceiver 240, or an image capturing or scanning device can receive or capture a signal or other information identifying information about a detector under test, including a type, manufacturer, or address of the detector. In some embodiments, responsive to the identifying information, the control circuitry 260 and programmable processor 260a can retrieve an appropriate configuration file from the memory device 250 for execution thereof. In some embodiments, responsive to the identifying information, the control circuitry 260 and programmable processor 260a can download an appropriate configuration file from a remote location, via the transceiver 240, for execution thereof. In some embodiments, the control software 260b can include a configuration file, and responsive to the identifying information, the control circuitry 260 and programmable processor 260a can execute the configuration file of the control software 260b based on the identifying information.

When executed, the configuration file can instruct the control circuitry 260 and programmable processor 260a how to cause the ambient condition or stimulus generating devices 220 to generate ambient conditions and stimuli, including in what combination and at what level and build-up rate, so as to initiate or cause an alarm in the detector under test. The devices 220 can generate and emit conditions and stimuli accordingly and direct any such emitted conditions and stimuli into the cup 210, which can direct any such emitted conditions and stimuli to the detector under test for detection thereof.

Although a few embodiments have been described in detail above, other modifications are possible. For example, the logic flows described above do not require the particular order described or sequential order to achieve desirable results. Other steps may be provided, steps may be eliminated from the described flows, and other components may be added to or removed from the described systems. Other embodiments may be within the scope of the invention.

From the foregoing, it will be observed that numerous variations and modifications may be effected without departing from the spirit and scope of the invention. It is to be understood that no limitation with respect to the specific system or method described herein is intended or should be inferred. It is, of course, intended to cover all such modifications as fall within the spirit and scope of the invention.

What is claimed is:
1. A system comprising:
one or more ambient condition or stimulus generating devices; and
a programmable processor,
wherein the programmable processor identifies a type and a manufacturer of a detector under test,
wherein the programmable processor searches a memory device for a local encrypted configuration file specific to the type of the detector under test, wherein the programmable processor locates a current encrypted configuration file on a remote cloud server associated with the manufacturer of the detector under test, wherein the programmable processor compares the local encrypted configuration file to the current encrypted configuration file and, absent a match therebetween, updates the local encrypted configuration file to match the current encrypted configuration file, wherein, when the programmable processor fails to locate the local encrypted configuration file specific to the type of the detector under test in the memory device, the programmable processor downloads the current encrypted configuration file specific to the type of the detector under test from the remote cloud server associated with the manufacturer of the detector under test and stores the current encrypted configuration file in the memory device as the local encrypted configuration file, wherein the local encrypted configuration file identifies a combination, a level, and a rate of a plurality of stimuli that cause an alarm in the detector under test, and wherein the programmable processor executes the local encrypted configuration file to cause the one or more ambient condition or stimulus generating devices to generate and emit the plurality of stimuli in the combination, at the level, and at the rate identified in the local encrypted configuration file.

2. The system of claim 1 further comprising:
a cup in fluid communication with the one or more ambient condition or stimulus generating devices,
wherein the one or more ambient condition or stimulus generating devices emit the plurality of stimuli into the cup, and
wherein the cup encloses a space around the detector under test to direct the plurality of stimuli to the detector under test.

3. The system of claim 1 further comprising:
a transceiver,
wherein the programmable processor receives the type and the manufacturer of the detector under test, via the transceiver, from the detector under test.

4. The system of claim 1 further comprising:
a transceiver,
wherein the programmable processor receives the type and the manufacturer of the detector under test, via the transceiver, from a control panel in communication with the detector under test.

5. The system of claim 1 further comprising:
a user interface device,
wherein the programmable processor identifies the type and the manufacturer of the detector under test from user input received by the user interface device.

6. The system of claim 1 further comprising:
an image capturing device,
wherein the programmable processor identifies the type and the manufacturer of the detector under test from an image or a scan of the detector under test obtained by the image capturing device.

7. A method comprising:
identifying a type and a manufacturer of a detector under test;
searching a memory device for a local encrypted configuration file specific to the type of the detector under test,
locating a current encrypted configuration file on a remote cloud server associated with the manufacturer of the detector under test,
comparing the local encrypted configuration file to the current encrypted configuration file and, absent a match therebetween, updating the local encrypted configuration file to match the current encrypted configuration file,
when the searching fails to locate the local encrypted configuration file specific to the type of the detector under test in the memory device, downloading the current encrypted configuration file specific to the type of the detector under test from the remote cloud server associated with the manufacturer of the detector under test and storing the current encrypted configuration file in the memory device as the local encrypted configuration file, the local encrypted configuration file identifying a combination, a level, and a rate of a plurality of stimuli that cause an alarm in the detector under test; and
executing the local encrypted configuration file to cause one or more ambient condition or stimulus generating devices to generate and emit the plurality of stimuli in the combination, at the level, and at the rate identified in the local encrypted configuration file.

8. The method of claim 7 further comprising:
receiving the type and the manufacturer of the detector under test, via a transceiver, from the detector under test.

9. The method of claim 7 further comprising:
receiving the type and the manufacturer of the detector under test, via a transceiver, from a control panel in communication with the detector under test.

10. The method of claim 7 further comprising:
identifying the type and the manufacturer of the detector under test from user input received by a user interface device.

11. The method of claim 7 further comprising:
identifying the type and the manufacturer of the detector under test from an image or a scan of the detector under test obtained by an image capturing device.

12. The method of claim 7 wherein the plurality of stimuli includes at least one of smoke, heat, and gas.

* * * * *